United States Patent [19]
Crainic

[11] Patent Number: 5,827,255
[45] Date of Patent: Oct. 27, 1998

[54] SANITARY NAPKIN COMPRISING AN ABSORBENT CORE HAVING A DENSITY GRADIENT

[75] Inventor: Sorin Crainic, Jouy-En-Josas, France

[73] Assignee: The Procter & Gamble Company, Cincinnati, Ohio

[21] Appl. No.: 791,094

[22] Filed: Jan. 27, 1997

Related U.S. Application Data

[63] Continuation of Ser. No. 374,742, Feb. 3, 1994, abandoned.

[30] Foreign Application Priority Data

Jul. 27, 1992 [EP] European Pat. Off. .............. 92306825

[51] Int. Cl.$^6$ ..................................................... A61F 13/15
[52] U.S. Cl. ............................................ 604/378; 604/368
[58] Field of Search ..................................... 604/368, 378, 604/385.1, 385.2, 367

[56] References Cited

U.S. PATENT DOCUMENTS 5,009,653 4/1991 Osborn, III .............................. 604/378
5,019,063 5/1991 Marsan et al. ........................... 604/378

FOREIGN PATENT DOCUMENTS 1182604 2/1983 Canada .................................... 604/378

*Primary Examiner*—John G. Weiss
*Assistant Examiner*—David J. Cho
*Attorney, Agent, or Firm*—Theodore P. Cummings; Jeffrey V. Bamber; Jacobus C. Rasser

[57] ABSTRACT

In a sanitary napkin, the retention layer of the absorbent core is covered by first tissue sheet of a density between 0.01 g/cm$^3$ and 0.1 g/cm$^3$ and by a second tissue sheet of a density between 0.08 and 0.3 g/cm$^3$, the difference in density between the tissue sheets being between 0.01 g/cm$^3$ and 0.2 g/cm$^3$. The density gradient on top of the retention layer results in a relatively high efficiency of the retention layer and in efficient draining of the topmost tissue sheet, so that chances of rewet are reduced.

2 Claims, 4 Drawing Sheets

000
SANITARY NAPKIN COMPRISING AN ABSORBENT CORE HAVING A DENSITY GRADIENT

This is a continuation of application Ser. No. 08/374,742, filed as PCT/US93/06694 Jul. 16, 1993 published as WO94/02093 Feb. 3, 1994, now abandoned.

FIELD OF THE INVENTION

The invention relates to sanitary napkin having a liquid pervious topsheet, a liquid-impervious backsheet and an absorbent core having a caliper of less than 5 mm, the absorbent core comprising a retention layer of absorbent material and at least a first and a second tissue sheet located between the retention layer and the topsheet.

BACKGROUND OF THE INVENTION

Such a sanitary napkin is known from the U.S. Pat. No. 5,009,653.

In this patent a sanitary napkin is described having a core consisting of a laminate of two air-laid tissue sheets between which a layer of hydro-gel forming material is comprised. The absorbent core is of relatively low caliper, for instance smaller than 2 mm. In order to improve the efficiency of the absorbent gelling material comprised in the core, a wipe acquisition sheet is located over the laminate, close to the topsheet, to improve lateral spread of liquids. The wipe acquisition sheet can be a 70%–30% rayon-polyester fiber sheet having a basis weight of 0.005 g/cm$^2$ and a thickness of about 0.04 cm and is available under the tradename SONTARA and marketed by E. I. DuPont Nemours Company.

Underneath the wipe acquisition sheet, a wet-laid tissue is located which serves to confine any loose absorbent gelling material, improves lateral wicking, provides some degree of absorbency and reduces the flow of fluids already absorbed in the absorbent core back to the topsheet. The wet-laid tissue has a basis weight of about 15.8 g/m2.

In the known sanitary napkin, retention of fluids in the upper tissue, which is located near the topsheet, can take place. This can lead to migration of body fluids from the upper tissue back through the topsheet (rewetting).

It is an object of the invention to provide a sanitary napkin of relatively small caliper and increased transport of fluids towards the retention layer and a relatively low chance of rewetting.

It is another object of the invention to provide a sanitary napkin having an improved fluid distribution and a relatively high effective capacity (capacity before soiling occurs).

SUMMARY OF THE INVENTION

The sanitary napkin according to the invention is characterized in that the first tissue sheet is located closest to the topsheet and has a density of between 0.01 g/cm$^3$ and 0.1 g/cm$^3$, the second tissue sheet being located closest to the retention layer and having a density of between 0.08 and 0.3 g/cm$^3$, the difference in density between the first and the second tissue sheet being between 0.01 g/cm$^3$ and 0.2 g/cm$^3$.

The density gradient between the upper and the lower tissue sheet causes the upper tissue sheet to be drained rapidly, the liquid being drawn from the upper tissue sheet by the suction which is exerted by the smaller capillaries of the lower and more dense tissue sheet. The upper tissue sheet is thereby quickly emptied and can receive subsequent gushes of liquids, so that the strike through rate of fluids passing through the topsheet into the absorbent core, is increased. Since the caliper of the tissue sheets is relatively small, the density gradient is established over a relative short distance, so that the capillary suction on the liquid exerted by the lower tissue sheet, effectively extends throughout the thickness of the whole of the upper tissue sheet.

The rapid draining of the upper tissue sheet and the consequent permanent availability of the upper sheet to absorb incoming liquids, increases the effective capacity of the sanitary napkin, wherein the 'effective capacity' is understood as the amount of liquid absorbed before soiling occurs by migration of liquids past the periphery of the napkin.

In the lower tissue sheet, the liquids are distributed in a lateral direction, the distributing capacity of the lower layer being relatively high, due to its high density. After distribution in the lower layer, the liquids are absorbed and retained in the lower retention layer, that preferably contains an absorbent gelling material.

From the U.S. Pat. No. 2 787 271, it is known to use in a sanitary napkin an upper layer of a relatively high absorbency and low density, and a lower layer having a higher degree of compression. The upper layer serves to provide a highly absorbing and soft contact surface for the wearer and lower layer acts as a fluid retention layer.

From DE-A-40 24 053 an absorbent product is know wherein a high density central layer (density of between 0.05 and 0.3 g/cm$^3$) is sandwiched between two outer, low density layers (density of between 0.005–0.1 g/cm$^3$) that form a unitary structure with the central layer. The layers consist of a mixture of thermoplastic fibers and air felt and are compressed to the desired density under application of heat. The product allegedly shows improved fluid absorption, fluid distribution and acquisition properties, especially for products having a caliper of about 2 mm. The known product fails to provide a number of tissue sheets overlying the retention layer, the tissue sheets establishing a density gradient for drawing fluids towards the retention layer.

From the English patent GB-A-2 089 214 a sanitary napkin is known having an upper layer of a density of 0.03 and 0.15 g/cm$^3$ and a lower layer of compressed cellulose having a density between 0.4 and 1.0 g/cm$^3$. The combination of the relatively open pore structure of the upper absorbent layer and the comparatively dense bottom layer, provides for rapid fluid transport through the top layer in a localised area and preferential absorption along the lower absorbent layer.

In the above structure the upper, lower density layer is relatively thick and functions to form a buffer between the lower, higher density layer in which the fluid is retained, and the wearer's body, to maintain a dry and comfortable feeling.

BRIEF DESCRIPTION OF THE DRAWINGS

Some embodiments of the sanitary napkin according to the invention will be described in detail with reference to the accompanying drawings.

DETAILED DESCRIPTIONS OF PREFERRED EMBODIMENTS

The present invention relates to female sanitary napkins and in particular to sanitary napkins which are thin and flexible and offer enhanced fit, comfort, and containment.

As used herein, the term "sanitary napkin" refers to an article which is worn by females adjacent to the pudendal region and which is intended to absorb and contain the various exudates which are discharged from the body (e.g., blood, menses and urine) and which is intended to be discarded after a single use (i.e., it is not intended to be laundered or otherwise restored or re-used). Interlabial devices which reside partially within and partially external of the wearer's vestibule are also within the scope of this invention. As used herein, the term "pudendal" refers to the externally visible female genitalia and is limited to the labia majora, the labia minora the clitoris, and the vestibule.

Figure 1:
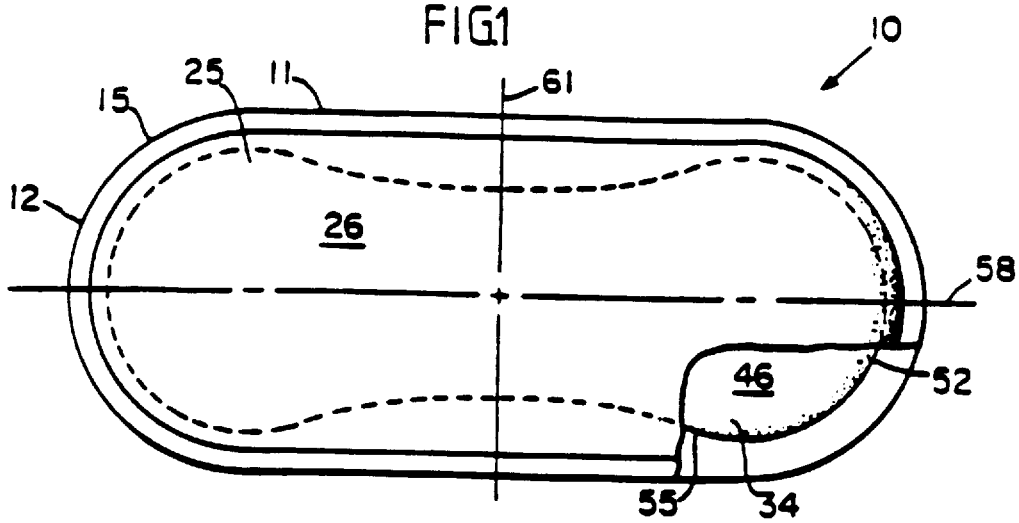
FIG. 1 shows a top plan view of a known sanitary napkin embodiment of the present invention with portions being torn away to show underlying structure.
Figure 2:
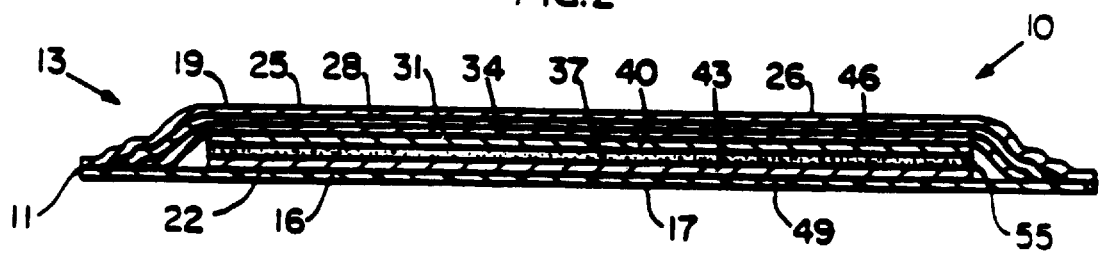
FIG. 2 shows a lateral cross-sectional view of the preferred sanitary napkin embodiment shown in FIG. 1 taken along line 2—2 of FIG. 1.

A preferred embodiment of a sanitary napkin 10 of the present invention is shown in FIGS. 1 and 2. As can be seen in FIGS. 1 and 2, a preferred sanitary napkin 10 basically comprises an absorbent core 13 and a liquid impermeable barrier means 16. The absorbent core 13 may be any means which is generally compressible, comfortable, nonirritating to the wearer's skin and capable of absorbing and containing body exudates such as menses, blood and urine. Preferably, the absorbent core 13 maintains integrity when wetted, in use. The absorbent core 13 has a first major surface 19 and a second major surface 22. The barrier means 16 is adjacent the second major surface 22 of the absorbent core 13. The barrier means 16 may be any means which is flexible and liquid impervious and which prevents the exudates absorbed and contained in the absorbent core 13 from wetting articles which contact the sanitary napkin 10 such as panties.

In the preferred embodiment shown in FIGS., 1 and 2, the absorbent core 13 is comprised of a liquid permeable topsheet 25, a liquid permeable sheet 28 of relatively low density, a tissue sheet 31 of relatively high density and a retention layer 34 having again a higher density than tissue sheet 28 and 31. In the preferred embodiment shown in FIGS. 1 and 2, the barrier means 16 is a barrier sheet. The retention layer 34 is comprised of hydrogel-forming material 37 disposed between two air-laid tissue sheets 40 and 43. The sanitary napkin 10 has side edges 11 and end edges 12 which together form the periphery 15 of the sanitary napkin 10. The sanitary napkin 10 has a body surface 26 which is generally defined by the topsheet 25 and a garment surface 17 which is generally defined by the barrier sheet 16.

Looking at some of the elements of the sanitary napkin 10 more specifically, the absorbent core 43 may be any means which is generally compressible, comfortable, non-irritating to the wearer's skin and capable of absorbing and containing body exudates. The absorbent core 13 has a first major surface 46, a second major surface 49, a pair of end edges 52 and a pair of side edges 55. The absorbent core 13 may be manufactured in a wide variety of sizes and shapes (e.g., rectangular, hourglass, etc.). A preferred shape of the absorbent core 13 is the dogbone shape shown in FIG. 1. This preferred absorbent core 13 is about 22.0 centimeters long (longitudinal dimension along the longitudinal centerline 58), about 7.0 centimeters wide across its midportion (lateral dimension along the lateral centerline 61) an about 8.0 centimeters wide across its widest portion (lateral dimension). The absorbent core 13 is in this embodiment symmetrically configured for ease of manufacture and so that no conscious effort is required by the wearer to properly place the napkin 10 in the direction it should be worn, and can also be asymmetrically configured The midportion is configured to basically conform to the wearer's thighs and to the thinner crotch portion of the wearer's panties so as to prevent excessive bunching. The size of the absorbent core 13 may be varied to accommodate wearers ranging in size and also ranging in the expected amount of exudate fluid volume. The absorbent core 13 may be attached over the core's first and second major surfaces 46 and 49, respectively, to adjacent members such as the topsheet 25 and barrier sheet 16 by any of the means well known in the art, such as by spray-glueing, lines, spots or spiral patterns of adhesive. Such attachment facilitates integrity and recoverability of the absorbent materials in use so as to maintain an optimum degree of absorbency. Preferably, the absorbent core 13 has a wet-tensile strength in the cross-direction of at least about 1 N per centimeter. Wet tensile strength is determinable by ASTM Standard D 829-49.

The retention layer 34 may be manufactured from a wide variety of liquid absorbent materials commonly used in disposable sanitary napkins, diapers, and other absorbent articles. Examples of suitable absorbent materials include comminuted wood pulp which is generally referred to as airfelt, creped cellulose wadding, absorbent foams, absorbent sponges, synthetic staple fibers, polymeric fibers, hydrogel-forming polymer gelling agents, or any equivalent materials or combinations of materials. A particularly preferred absorbent material are polymeric gelling agents. Polymeric gelling agents are those materials which, upon contact with fluids (i.e., liquids) such as water or body fluids, imbibe such fluids and thereby form hydrogels. In this manner, fluid discharged into the absorbent core 34 can be acquired and held by the polymeric gelling agent, thereby providing the articles herein with enhanced absorbent capacity and/or improved fluid retention performance.

The polymeric gelling agent which is employed in the retention layer 34 will generally comprise particles of a substantially water-insoluble, slightly cross-linked partially neutralized, hydrogel-forming polymer material. Such polymer materials can be prepared from polymerizable, unsaturated, acid-containing monomers. Suitable unsaturated acidic monomers for use in preparing the polymeric gelling agents used in this invention include those listed in U.S. Pat. No. 4,654,039, entitled "Hydrogel-Forming Polymer Compositions For Use In Absorbent Structures", which issued to Brandt, Goldman and Inglin on Mar. 31, 1987, and which patent is incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

In the hydrogel-forming polymeric gelling agent the polymeric component formed from unsaturated acid-containing monomers may be grafted onto other types of polymer moieties such as starch or cellulose. Polyacrylate grafted starch materials of this type are especially preferred for use herein.

Preferred polymer gelling agents which can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric gelling agents used in the retention layer 34 herein, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in the U.S. Pat. No. 4,076,663, which patent issued to Masuda et al. on Feb. 28, 1978, and which patent is incorporated herein by reference. Preferred cross-linking agents are the di- or polyesters of unsaturated mono- or polycarboxylic acids with polyols, the bisacrylamides and the di- or tryallyl amines. Especially preferred cross-linking agents are N,N'-methylenebisacrylamide, trimethylol propane triacrylate and triallyl amine. The cross-linking agent can generally comprise from about 0.001 mole percent to 5.0 mole percent of the resulting hydrogel-forming polymer material. More preferably, the cross-linking agent will comprise from about 0.01 mole percent to 3.0 mole percent of the hydrogel-forming polymeric gelling agent used herein.

The slightly cross-linked, hydogel-forming polymeric gelling agents which may be used in the articles of the present invention are generally employed in their partially neutralized form. For purposes of this invention, such materials are considered partially neutralized when at least 25.0 mole percent, and preferably at least 50.0 mole percent of monomers used to form the polymer are acid group-containing monomers which have been neutralized with a salt-forming cation. Suitable salt-forming cations include alkali metal, ammonium, substituted ammonium, and amines. This percentage of the total monomer utilized which are neutralized acid group-containing monomers is referred to herein as the "degree of neutralization".

The polymeric gelling agent materials used in the absorbent articles herein must have a relatively high capacity for imbibing fluids encountered in such articles. The absorbent capacity of these materials can be quantified by referencing the "gel volume" of the polymeric gelling agents which are to be selected for use in the present invention.

For purposes of this invention, gel volume can be defined in terms of the amount of synthetic urine absorbed by any given polymeric gelling agent and is specified as grams of synthetic urine per gram of polymeric gelling agent. Gel volume in synthetic urine can be determined by forming a suspension of about 0.1–0.2 parts of dried polymeric gelling agent to be tested with about 20 parts of synthetic urine. This suspension is maintained at ambient temperature under gentle stirring for a time sufficient, e.g., about 1 hour, for swelling equilibrium to be attained. The gel volume of the polymeric gelling agent in grams of synthetic urine per gram of polymeric gelling agent is then calculated from the weight fraction of the polymeric gelling agent in the suspension and the ratio of the liquid volume excluded from the formed hydrogel to the total volume of the suspension.

The gel volume of the gelling agent used in the retention layer 34 herein will generally be at least about 20.0 grams of synthetic urine per gram of polymeric gelling agent. More preferably, the gel volume of the materials employed will range from about 20.0 to about 35.0 grams of synthetic urine per gram of polymeric gelling agent.

Within the webs which form the layers of the retention layer, or core, 34, the particles of the polymeric gelling agent should be thoroughly dispersed but may or may not be uniformly distributed. In particular, there may be regions or zones of the core layers which have higher concentrations of gelling agent particles than do other regions or zones of the layers.

In a preferred embodiment, the sanitary napkin 10 of the present invention will have a hydrogel forming polymeric gelling agent distributed throughout at least about 17.0 square centimeters of the napkin, more preferably throughout at least about 50.0 square centimeters of the napkin, and most preferably throughout the whole surface area of the core. Preferably, the hydrogel-forming polymeric gelling agent will be distributed in an amount of from about 0.001 grams per square centimeter to about 0.009 grams per square centimeter, more preferably of from about 0.003 grams per square centimeter to about 0.008 grams per square centimeter, and most preferably from about 0.004 grams per square centimeter to about 0.007 grams per square centimeter. Preferably, the absorbent core 34 will contain from about 5.0% to about 85.0% by weight of hydrogel-forming polymeric gelling agent, more preferably from about 10.0% to about 70.0%, and most preferably from about 15% to about 55.0%.

In the preferred embodiment shown in FIG. 2, the retention layer 34 is a laminate comprised of a layer of superabsorbent polymer material 37 disposed between two airlaid tissues 40 and 43. A suitable laminate is the superabsorbent laminate WATER-LOCK L-535 available from the Grain Processing Corporation fo Muscatin, Iowa (WATER-LOCK registered TM by Grain Processing Corporation). Such superabsorbert laminates are disclosed in U.S. Pat. No. 4,467,012, entitled "Composition For Absorbent Film And Method Of Preparation", which patent issued to Pedersen et al. on Aug. 21, 1984, and U.S. Pat. No. 4,260,443, entitled "Laminated Absorbent Process", which patent issued to Lindsay et al. on Apr. 7, 1981, and which patents are incorporated herein by reference. The WATER-LOCK L-535 has a hydrogel polymer loading of 0.005 grams per square centimeter, however, loadings of 0.001–0.009 grams per square centimeter have been found acceptable. The first and second tissue layers 40 and 43 provide containment of the superabsorbent polymer material 37, improve lateral wicking of the absorbed exudates throughout the retention layer 34 and provide a degree of absorbency. In the case of non-particulate hydrogel-forming polymer gelling agents which can be formed into fibrous sheets, foams or films, the non-particulate gelling agent may comprise from about 15% to about 100% by weight of the retention layer 34, more preferably of from about 40% to about 100% and most preferably of from about 60% to about 100%. The basis weight of such non-particulate superabsorbents may be from about 0.002 to about 0.028 grams per square centimeter, more preferably of from about 0.003 to about 0.018, and most preferably of from about 0.004 to about 0.010. Two suitable and commercially available non-particulate absorbent materials for the retention layer 34 are a double layer acrylic fibrous material available under the tradename Lanseal F from the Choli Company, LTD., of Higashi, Osaka Japan and a carboxymethylcellulose fibrous material available under the tradename Aqualon C from Hercules, Inc. of Wilmington, Del.

The total absorbent capacity of the absorbent core 13 should be compatible with the design exudate loading for the intended use of the sanitary napkin 10. Further the absorbent capacity of the absorbent core 13 may be varied to accommodate wearers ranging in the expected amount of exudate fluid volume. For instance, a different absorbent capacity may be utilized for sanitary napkins intended for daytime use as compared with those intended for night-time use, or for sanitary napkins intended for use by teenage females as compared with those intended for use by more mature women.

It should be noted that the scope of the present invention is intended to extend to sanitary napkins which are void of any superabsorbent material and which have a central retention layer overlayed solely by nonwoven material, wherein the nonwoven materials have caliper of less that 0.50 millimeters, as determined by the caliper test, as later defined.

To illustrate the effect on the fluid distribution of two tissue sheets of different density overlying the retention layer 34, a partitioning test was carried out. The test method and the results are discussed here after.

Partitioning Test

Four different layered absorbent structures were produced, each structure comprising three tissue sheets of different densities, the lower tissue sheet functioning as the retention layer. The tissue sheets used in the structures have the following physical properties:

| Tissue Type | Caliper (mm) | Density |
|---|---|---|
| A, air laid | 0.8 | 0.08 |
| B, air laid | 0.8 | 0.087 |
| C, air laid | 0.8 | 0.094 |
| D, air laid | 0.5 | 0.10 |
| E, air laid | 0.4 | 0.12 |
| F, air laid | 0.5 | 0.11 |
| G, air laid | 0.4 | 0.14 |
| H, wet laid | 0.2 | 0.20 |
| I, wet laid | 0.2 | 0.21 |
| J, available from J.W.SUOMINEN OY, POB 25, SF-29251 NAKKILA Finland under the trade name FIBERELLA. | | |

The combination of tissue sheets used in the partitioning test were: AGH, BFI, CDE and JDD.

Figure 3:
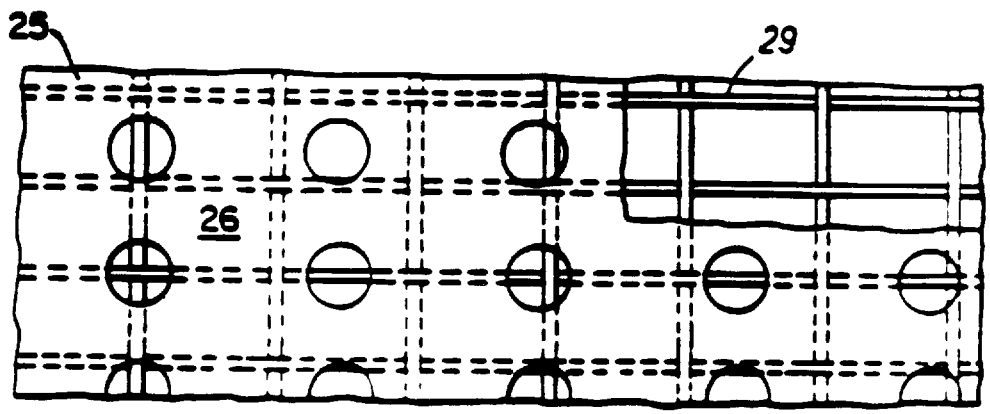
FIG. 3 shows a top plan view of a known topsheet and wipe acquisition sheet laminate with portions of the topsheet being torn away to show underlying structure.

The structure JDD is of a type similar to that as described in U.S. Pat No. 5,009,653, wherein the tissue of type J was an open, net-like structure as shown under reference numeral 29 of FIG. 3.

For each tissue the capacity was measured by immersion of each tissue in Paper Industrial Fluid for 20 minutes, followed by uniform application of a pressure of 35 g/cm$^2$ for 2 minutes on each tissue.

The composition of the Paper Industrial Fluid is:

| | |
|---|---|
| Glycerol | 80 g/l |
| Na Cl | 10 g/l |
| Na HCO$_3$ | 4 g/l |
| CMC type C-5678 available from Sigma Chemie GmbH, Grünwalder Weg 30, 8024 DEISENHOFEN, GERMANY | 18 g/l |

Each tissue was cut into a 10.2 cm×10.2 cm patch, which was weighed with an accuracy of 0.001 g. Three patches were superimposed each time to obtain four different layered structures AGH, BFI, CDE and JDD. Each layered structure was covered by a plexiglass plate of a 10.2 cm×10.2 cm surface having a 15 mm×3.5 mm oval hole in the center. A weight of 3636 g was applied to the plexiglass plate so that a pressure of 35 g/cm$^2$ was exerted on the tissues.

The total theoretical capacity of each layered structure was calculated by adding the theoretical capacities of each single layer in the structure.

With a pipette 5% of the above calculated total capacity of the layered structure was deposited onto the topmost layer. Three minutes after deposition of the fluid, each layer was weighed separately.

An additional 5% load was applied to reach 10% of each layered structure's total capacity and each layer was again weighed after allowing the Paper Industrial Fluid to settle for three minutes. This procedure was repeated to reach a loading of 20%, 30%, 50%, 70%, 90% and 100% of the structure's total capacity. After each incremental load, three minutes were allowed after which time lapse the weight measurement was performed within 1 minute.

The procedure was repeated for three samples for each layered structure and the results were averaged over these three samples.

Figure 6:
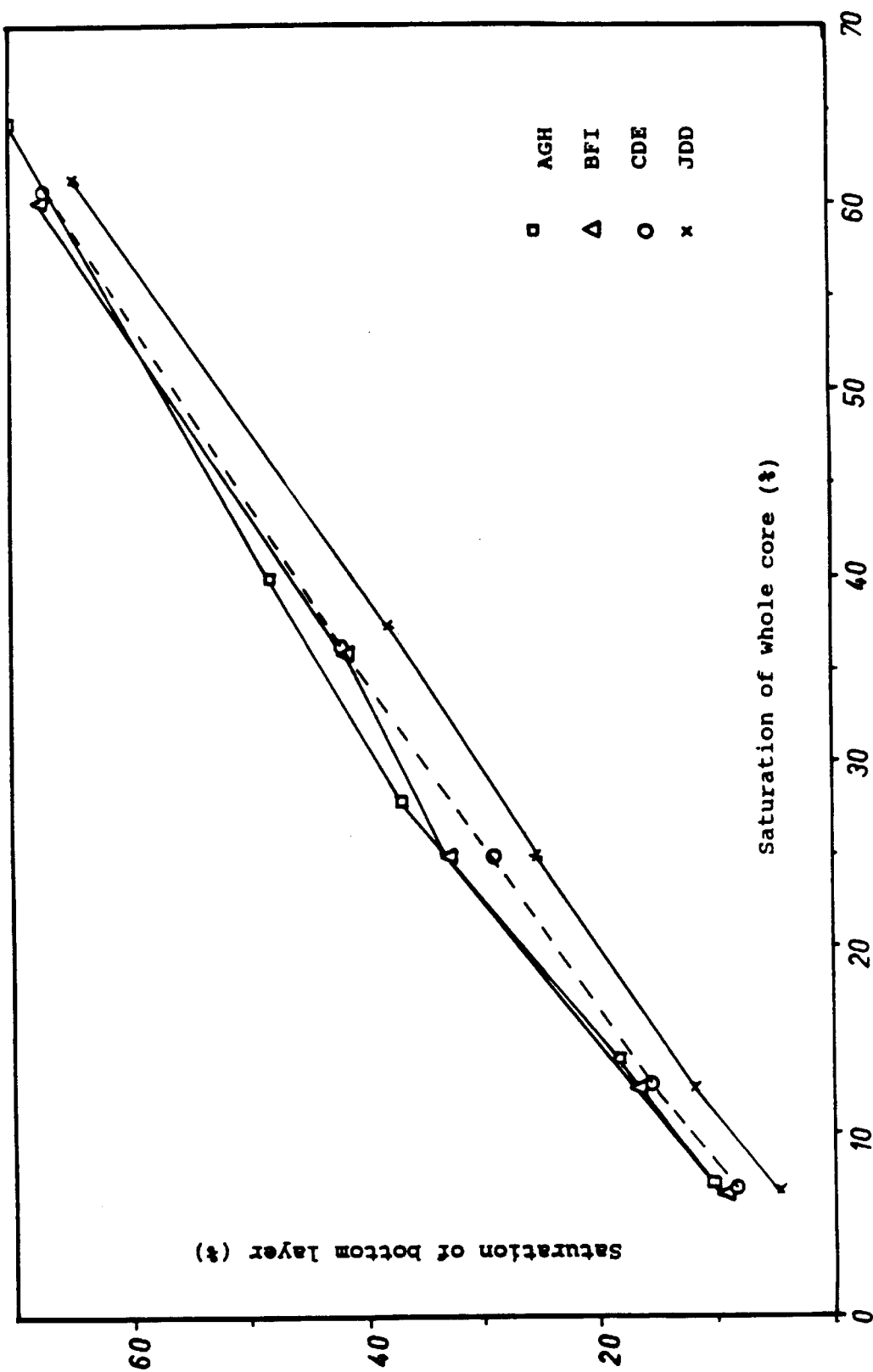
FIG. 6 shows a graph of the percentage saturation of the bottom layer in a three-layered structure according to the invention compared to a known three-layered structure.
Figure 7:
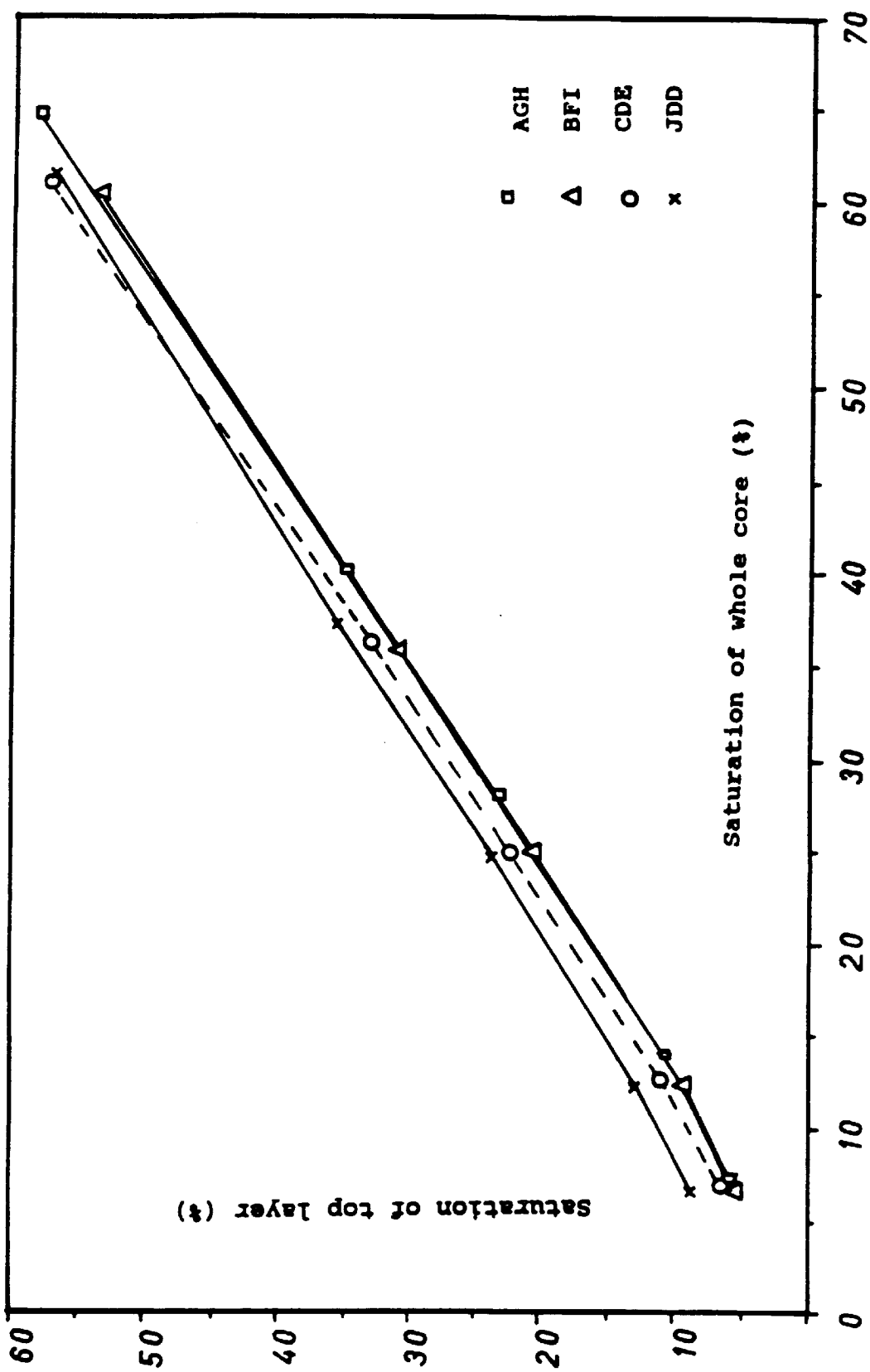
FIG. 7 shows a graph of the percentage saturation of the top layer in a three-layered structure according to the invention compared to a known three-layered structure.

The measurement results as shown in FIGS. 6 and 7 are the percentage saturation of the top, or bottom layer versus the percentage saturation of the total layered structure. The figures for the percentage saturation of the layered structure as a whole was each time determined by the sum of the amounts of liquids present in each layer, divided by the final actual amount absorbed at the end of the test, to take into account any losses of liquid during measurement.

From FIG. 6 it can be seen that the known reference layered structure, consisting of tissues JDD, results in the lower amount of saturation of the lower layer. The Fiberella upper layer, indicated as "J" is a net-like fabric, having a mesh size of about 1 mm$^2$, the density of the fabric at the position of the strands being relatively high (about 0.1 g/cm$^3$). Tissues of this type are useful for promoting lateral spread of liquids across the absorbent core. From FIGS. 6 and 7 it appears that an absorbent retention layer covered by two layers, of which the one nearest to the retention layer has the higher density, (structure AGH, BFI and CDE) acquires more liquid that a retention layer which is covered by two layers as are known from U.S. Pat. No. 5,009,653 (structure JDD) and that therefore the efficiency of the bottom layer is increased. From FIG. 7 it appears that for the structures AGH, BFI and CDE, the upper layer retains less liquid because it is drained by the underlying more dense layer, and that the chance of rewet is reduced.

Superimposed over the tissue sheets 22 and 31 is the liquid permeable topsheet 25. In a preferred embodiment, the topsheet 25 is associated with the upper tissue by spray-gluing the topsheet 25 to the surface of the sheet 28. The topsheet 25 is compliant, soft feeling, and non-irrating to the wearer's skin. Further the topsheet 25 is liquid pervious, permitting a liquid to readily transfer through its thickness. A suitable topsheet 25 may be manufactured from a wide range of materials such as polymeric materials, formed thermoplastic films, apertured plastic films, porous foams, reticulated foams, natural fibers (e.g., wood or cotton fibers), synthetic fibers (e.g., polyester or polypropylene fibers) or from a combination of natural and synthetic fibers, with apertured formed films being preferred. Formed films are preferred for the topsheet 25 because the are pervious to liquids and yet non-absorbent. Thus, the surface of the formed film which is in contact with the body remains dry, thereby reducing body soiling and creating a more comfortable feel for the wearer. Suitable formed films are described un U.S. Pat. No. 3,929,135, entitled "Absorptive Structure Having Tapered Capillaries", which patent issued to Thompson on Dec. 30, 1975, U.S. Pat. No. 4,324,246, entitled "Disposable Absorbent Article Having A Stain Resistant Topsheet", which patent issued to Mullane and Smith on Apr. 13, 1982, U.S. Pat. No. 4,342,314, entitled "Resilient Plastic Web Exhibiting Fiber-Like Properties", which patent issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which patent issued to Ahr, Louis, Mullane, and Ouellete on Jul. 31, 1984, all of which patents are incorporated herein by reference.

In a preferred embodiment of the present invention, the body surface 26 of the topsheet 25 is hydrophilic. The hydrophilic body surface 26 helps liquid to transfer through the topsheet 25 faster than if the body surface 26 was not hydrophilic. This diminishes the likelihood that menstrual fluid will flow off the topsheet 25 rather than being absorbed by the absorbent core 13. In a preferred embodiment, the body surface 26 of the topsheet 25 is made hydrophilic by treating the body surface 26 with a surfactant. It is preferred that the surfactant be substantially evenly and completely distributed throughout the body surface 26 of the topsheet 25. This can be accomplished by any of the common techniques well known to those skilled in the art. For example, the surfactant can be applied to the topsheet 25 by spraying, by padding, or by the use of transfer rolls. Further, the surfactant can be incorporated into the polymeric materials of a formed film topsheet or between or within the fiber of a nonwoven topsheet.

The barrier means 16 is adjacent the second major surface 22 of the absorbent core 13. In a preferred embodiment the absorbent core 13 may be affixed over the second major surface 22 of the absorbent core 13 to the barrier means 16. Any of the common techniques well known in the art, such as spray-glueing, spiral glueing or lines or spots of adhesive may be used for this purpose. The barrier means 16 generally defines the garment surface 17 of the sanitary napkin 10. The barrier means 16 may be any means which is impervious to liquids and which prevents exudates absorbed and contained in the absorbent core 13 form soiling articles such as panties, which come in contact with the garment surface 17 of the sanitary napkin 10. In the preferred embodiment of the sanitary napkin 10 illustrated in FIGS. 1 and 2, the barrier means 16 is a barrier sheet manufactured from a thin plastic film. Other flexible liquid impervious materials may also be used. Preferably, the barrier sheet 16 is a polyethylene film having a thickness of from about 0.012 millimeter to about 0.051 millimeter. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The barrier sheet 16 is preferably embossed and/or matte finished to provide a more clothlike appearance. Further, the barrier sheet 16 may permit vapors to escape from the absorbent core 13 while still preventing exudates from passing through the barrier sheet 16.

Preferably, the topsheet 25 and the barrier sheet 16 have length and width dimensions generally larger than the absorbent core 13 so that they extend beyond the edges 52 and 55 of the absorbent core 13 where they are associated together in a suitable manner. As used herein, the term "associated" encompasses configurations whereby a first member is directly joined to a second member and configurations whereby a first member is indirectly joined to a second member by affixing the first member to intermediate members which in turn are affixed to the second member. The extension of the topsheet 25 and/or the barrier sheet 16 beyond the core end edges 52 and the core side edges 55 of the absorbent core 13 form the end edges 11 and the side edges 12, respectively, of the sanitary napkin 10. In an embodiment, the barrier sheet 16 and the topsheet 25 have an elliptical shape and extend beyond the absorbent core 13 a distance of at least about 1.0 centimeter where they are joined directly to each other by attachment means as are well known in the art. the attachment means may be, for example, a uniform continuous layer of adhesive a patterned layer of adhesive, or an array of separate lines or spots of adhesives, or heat and pressure bonding.

The sanitary napkin 10 of the present invention has a low flexure-resistance. Thus, the sanitary napkin 10 of the present invention is highly flexible and conforms very well to the various shapes of the female urogenital region. Preferably, the sanitary napkin 10 of the present invention has a fluxure-resistance of less than about 300.0 grams, more preferably less than about 250.0 grams and still, more preferably less than about 175.0 grams and most preferably about 160 grams.

The flexure-resistance of a sanitary napkin is measured by peak bending stiffness. Peak bending stiffness is determined by a test which is modeled after the ASTM D 4032.82 CIRCULAR BEND PROCEDURE, as is described in detail in U.S. Pat. No. 5,009,653.

As previously mentioned, the sanitary napkin 10 of the present invention has a liquid capacity great enough to absorb medium to high menstrual flows. Two capacities, which, depending on the size of the sanitary napkin may be the same, are determinable: test capacity and total capacity. Preferably, the napkin 10 of the present invention has a test capacity of at least about 8.0 grams, more preferably of at least about 15.0 grams, and most preferably of at least about 18.0 grams.

Preferably, the napkin 10 of the present invention has a total capacity of at least about 20.0 grams, more preferably of at least about 30.0 grams, and most preferably of at least about 40.0 grams.

The test and total capacities of a sanitary napkin are determined as follows. Any panty adhesive release paper is removed form the napkin to be tested. to determine test capacity, a 4.75×14.0 centimeters portion of any other configuration having 66.5 square centimeters, of the sanitary napkin is cut from the portion of the sanitary napkin which would be centered under the vaginal orifice when the sanitary napkin is worn. Total capacity is determined using the entire napkin minus any release paper. The article is weighed to the nearest 0.1 gram. The article is then submerged in a beaker of sterile saline (obtainable form the Baxter Travenol Company of Deerfield, Ill.), such that the article is totally submerged and is not bent or otherwise twisted of folded. The article is submerged for 10 minutes. The article is removed from the saline and suspended for two minutes in a vertical position to allow the saline to drain out the article. The article is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article, whichever the case may be.

Because of the flexibility requirements of the sanitary napkins 10 of the present invention, it is likely that the sanitary napkins 10 will be relatively thin. It is preferred to keep the sanitary napkins 10 of the present invention thin so that the sanitary napkins 10 of the present invention will be unobtrusive and the user will have a low awareness of the sanitary napkin 10 of the present invention while it is being worn. The sanitary napkin 10 shown in FIGS. 1 and 2 has a caliper of about 1.9 millimeters. The caliper of a sanitary napkin 10 is determined by the following test.

A comparator gauge, and specifically the Ames, Model 130 with dial indicator Model 482, available from the B. C. Ames, Company of Waltham, Mass. is needed. The comparator gauge should have a circular comparator foot made of aluminum and having a weight of 10.0 grams and a contact surface of 5.16 square centimeters. The comparator gauge is zeroed. An 80.0 grams stainless steel weight is placed on the spindle extending above the comparator dial. The comparator foot is raised and the napkin, with any panty adhesive release paper being removed, is placed garment surface down on the base plate. The napkin is positioned on the base plate so that when the foot is lowered it is in the center of the napkin. Try to smooth out or avoid any wrinkles in the napkin. Gently lower the foot onto the napkin. Determine the napkin caliper by reading the comparator dial 30 seconds after the foot comes in contact with the napkin. Repeat the measurement 3.0 centimeters form each of the ends of the absorbent material along the longitudinal centerline 58 of the napkin. The average of the three readings is the caliper of the sanitary napkin. Preferably, the sanitary napkins 10 of the present invention have a caliper of less than about 3.5 millimeters, more preferably less than about 2.5 . millimeters, and most preferably less than about 2.0 millimeters.

Figure 4:
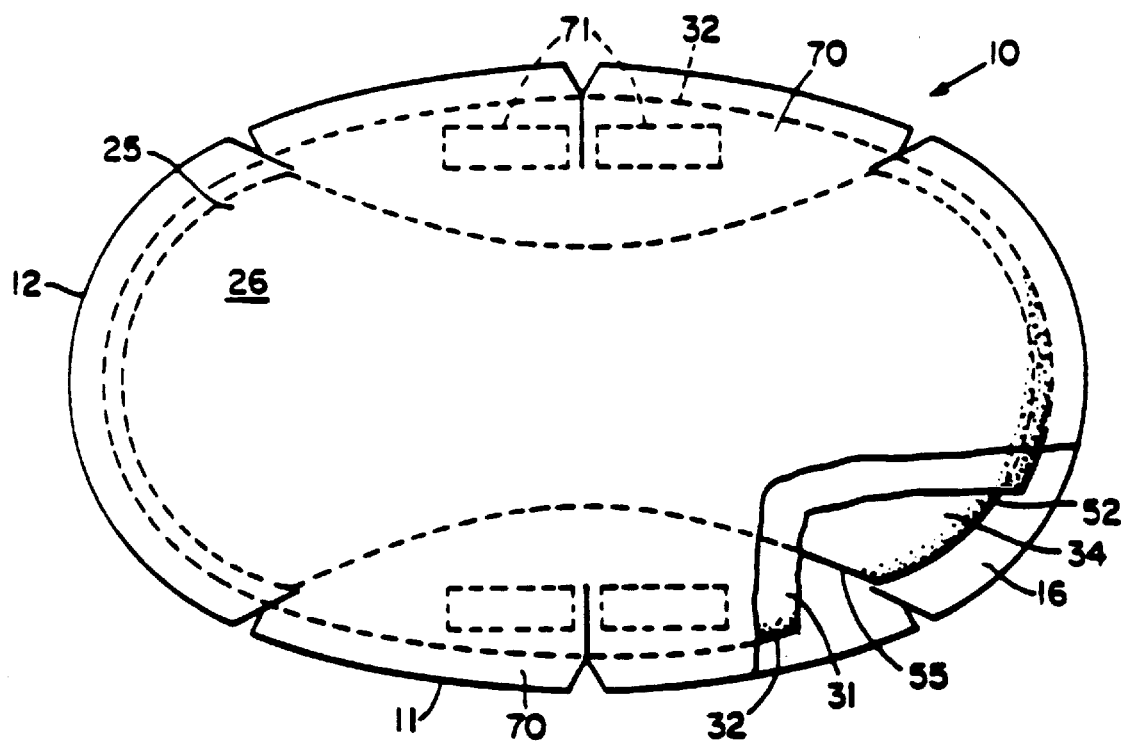
FIG. 4 shows a top plan view of an alternatively preferred sanitary napkin embodiment of the present invention with portions being torn away to show underlying structure.

An alternative embodiment of a sanitary napkin 10 of the present invention is shown in FIG. 4. In this embodiment, the sanitary napkin 10 has two flaps 70 each of which are adjacent to and extend laterally from a side edge of 55 of the absorbent core 13. The flaps 70 are configured to drape over the edges of the wearer's panties in the crotch region so that the flaps 70 are disposed between the edges of the wearer's panties and the wearer's thighs. The flaps 70 serve at least two purposes. First, the flaps 70 help serve to prevent soiling the wearer's body and panties by menstrual fluid. Second, the flaps 70 are preferably provided with attachment means 71 on their garment surface 17 so that the flaps 70 can be folded back under the panty and attached to the garment facing side of the panty. In this way, the flaps 70 serve to keep the napkin 10 properly positioned in the panty. A preferred attachment means 71 is a pressure-sensitive adhesive, as is well known in the art. Alternatively, the flaps 70 may be attached to each other on the underside of the panty by the attachment means 71 without being affixed to the panty.

A number of sanitary napkins having flaps suitable or adaptable for use with the sanitary napkins 10 of the present invention are known. such flaps are disclosed in U.S. Pat. No. 4,687,478, entitled "Shaped Sanitary Napkin With Flaps", which patent issued to Van Tilburg on Aug. 18, 1987, U.S. Pat, No. 4.608,047 entitled "Sanitary Napkin Attachment Means", which patent issued to Mattingly on Aug. 26, 1986, U.S. Pat. No. 4,589,876, entitled "Sanitary Napkin", which patent issued to Van Tilburg on May 20, 1986, and U.S. Pat. No. 4,285,343, entitled "Sanitary Napkin", which patent issued to McNair on Aug. 25, 1981, all of which patents are incorporated herein by reference.

Figure 5:
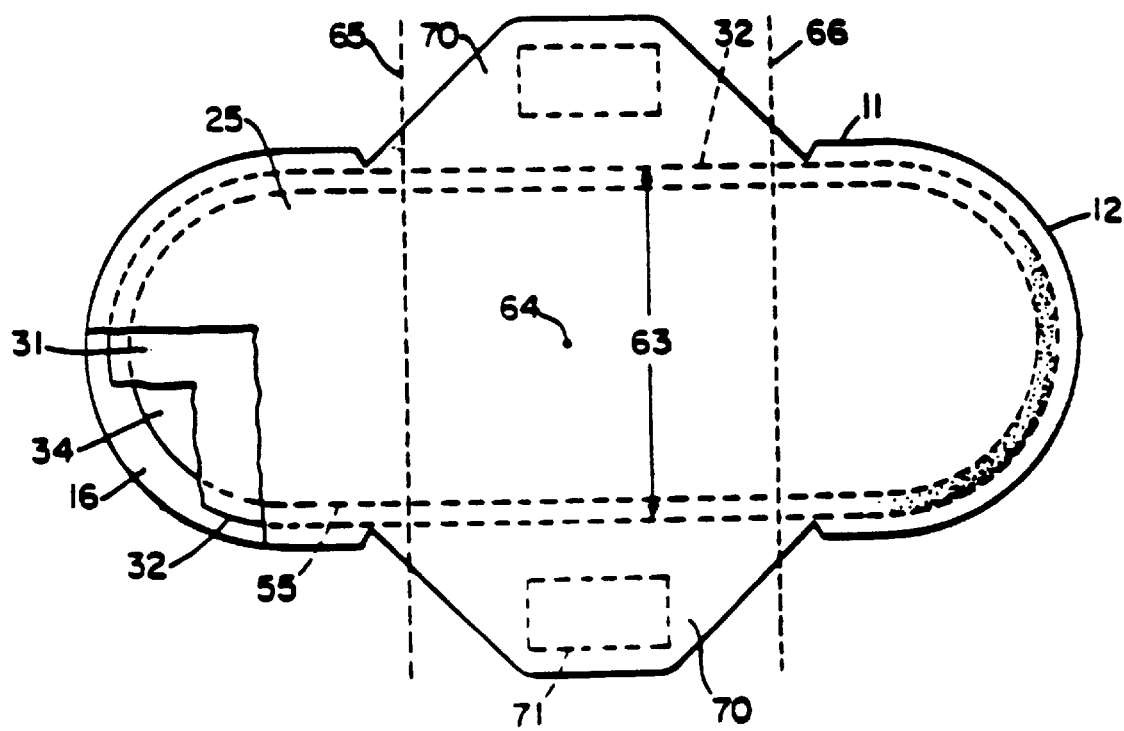
FIG. 5 shows a top plan view of another alternatively preferred sanitary napkin embodiment of the present invention with portions being torn away to show underlying structure.

Another alternative embodiment of a sanitary napkin 10 of the present invention is shown in FIG. 5. Like the napkin 10 shown in FIG. 4, this, napkin 10 also has flaps 70, only of a different configuration. In this embodiment, the flaps 70 are comprised only of the topsheet 25 and the barrier sheet 55.

What is claimed is:

1. A sanitary napkin, comprising:

a liquid pervious topsheet;

a liquid impervious backsheet attached to the topsheet; and an absorbent core positioned between the topsheet and the backsheet having i) a first tissue sheet having capillaries, said first tissue sheet being positioned adjacent to the topsheet and having a density from about 0.01 $g/cm^3$ to about 0.1 $g/cm^3$;

ii) a second tissue sheet having capillaries, said second tissue sheet being positioned adjacent to and below the first tissue sheet and having a density of from about 0.08 $g/cm^3$ to about 0.3 $g/cm^3$, the difference in density between the first and the second tissue sheets being from about 0.01 $g/cm^3$ to about 0.2 $g/cm^3$;

iii) a density gradient formed between the first tissue sheet and the second tissue sheet positioned adjacent to one-another such that fluid impacting the first tissue sheet will be drawn from the first tissue sheet by suction exerted by the smaller capillaries of the lower and more dense second tissue sheet; and iv) a retention layer positioned between the second tissue sheet and the liquid impervious backsheet, said retention layer storing the fluid drawn by the gradient formed by the first tissue sheet and the second tissue sheet.

2. A sanitary napkin according to claim 1, wherein said retention layer comprises a laminate of two retention tissue sheets between which a layer of absorbent gelling material is interposed.

* * * * *